United States Patent [19]
Sauvageau et al.

[11] Patent Number: 5,457,983
[45] Date of Patent: Oct. 17, 1995

[54] APPARATUS AND METHOD FOR PRODUCING A REFERENCE GAS

[75] Inventors: Mario A. Sauvageau, Dollard-des-Ormeaux; Jean Béliveau, Longueuil; Lysane Lavoie, Montréal; Richard Gilbert, Roxboro, all of Canada

[73] Assignee: Tecnovir International Inc., Quebec, Canada

[21] Appl. No.: 293,944

[22] Filed: Aug. 23, 1994

[51] Int. Cl.⁶ .................................................. G01N 31/06
[52] U.S. Cl. ............................................................. 73/1 G
[58] Field of Search .................................. 73/1 G, 23.21

[56] References Cited

U.S. PATENT DOCUMENTS

| | | | |
|---|---|---|---|
| 3,290,920 | 12/1966 | Novak | 73/1 G |
| 3,760,773 | 9/1973 | Christensen | 73/1 G |
| 3,902,851 | 9/1975 | Dravnieks | 23/254 R |
| 4,036,915 | 7/1977 | Lucero et al. | 73/1 G |
| 4,063,446 | 12/1977 | Fuhrmann | 73/1 G |
| 4,934,386 | 6/1990 | Walker et al. | 131/329 |
| 4,998,433 | 3/1991 | Stumpf et al. | 73/25.01 |
| 5,027,145 | 6/1991 | Samuels | 354/299 |
| 5,157,957 | 10/1992 | Mettes et al. | 73/1 G |

OTHER PUBLICATIONS

Benignus, Vernon A. and James D. Prah, "A computer-controlled vapor-dilution olfactometer", in Behavior Research Methods & Instrumentation, 1980, vol. 12 (5), pp. 535-540.

Cain, William S. et al., "Ventilation requirements in buildings—I., Control of occupancy odor and tobacco smoke odor", in Atmospheric Environment, 1983, vol. 17, No. 6, pp. 1183-1197.

Stordeur, R. T. et al., "A new microprocessor-controlled dynamic olfactometer", in Journal of the Air Pollution Control Association, Apr. 1981, vol. 31, No. 4, pp. 377-380.

Walker, James C. et al., "Apparatus for the automated measurement of the responses of humans to odorants", in Chemical Senses, 1990, vol. 15, No. 2, pp. 165-177.

Designation: E 544-75 (Reapproved 1988), "Standard practices for referencing suprathreshold odor intensity", American Society for Testing and Materials.

Sweeten, John M. et al., "A butanol olfactometer for field measurement of ambient odors", in Journal of the Air Pollution Control Association, Dec. 1984, vol. 34, No. 12, pp. 1208-1213.

*Primary Examiner*—Robert Raevis
*Attorney, Agent, or Firm*—Lowe, Price, LeBlanc & Becker

[57] ABSTRACT

The apparatus and the method are provided for the generation of a reference gas consisting of a gaseous medium carrying a known concentration of vapors of a volatile liquid substance. The gaseous medium is introduced into a container enclosing an absorbing material filled with the volatile liquid substance for obtaining a mixed gas. The mixed gas is cooled with thermoelectric Peltier cells in a condenser to a given temperature lower than the temperature of the mixed gas in the container for condensing a part of the vapors. Condensates of the vapors fall back by gravity towards the container. A temperature probe at the outlet and a cooling control device are used for maintaining the mixed gas at the outlet at the given temperature. The apparatus is particularly useful for suprathreshold odor intensity olfactometers, gas calibrators and in medicine.

20 Claims, 5 Drawing Sheets

APPARATUS AND METHOD FOR PRODUCING A REFERENCE GAS

FIELD OF THE INVENTION

The present invention relates to an apparatus and a method for generating a reference gas consisting of a gaseous medium carrying a known concentration of vapors of a volatile liquid substance.

BACKGROUND OF THE INVENTION

The generation of a reference gas having a known concentration of a volatile liquid substance is very useful, for instance, in the art of gas calibration, olfactometry and medicine.

Gas calibrators are widely used by laboratories and industries for the calibrations of sensors or other analytical equipments. Such gas calibrators usually use a permeation device, such as the one described in U.S. Pat. No. 4,399,942 (Chand) issued on Aug. 23, 1983.

Olfactometers are used for helping panelists to compare and evaluate odor intensities. In fact, odors are difficult to classify and to measure with automatic devices because most odors are issued from complex chemical compositions. The nuisance of an odor often results from a synergetic effect between odor pollutants and the only practical method for globally evaluating the odor nuisance is the use of a human test panel along with an olfactometer.

For decades, the sensory technique for measuring odors was the threshold method. This method typically involves the sampling of the odor pollutants into hermetical bags and the laboratory testing thereof by submitting the samples to dilution with odorless air until at least half of the members of a panel cease to perceive the odor pollutants in the diluted sample. The relative intensity of the odor pollutants are then deducted from the numbers of dilutions of the original samples. The number of dilutions is the figure used as a reference for quantifying the nuisance.

Because the threshold of the human nose is an extreme of sensitivity, it varies from a person to another and also for the same person subjected to different environmental conditions. Therefore, the threshold technique is not very accurate.

To achieve better results, a large number of panelists is required through the use of statistical methods, thus requiring considerable time and resources to perform a threshold analysis of a single mixture. One alternative way for evaluating the odor nuisance is to provide air samples and compare them with a reference gas carrying a known concentration of a reference substance with a clearly experienceable specific odor. In this technique, known as suprathreshold odor referencing, dilutions of the reference gas are achieved until both odors are believed to be equivalent by a panelist. The concentration of the reference gas is then recorded for comparing with the results of the other panelists. The practices for referencing the odor intensity in the suprathreshold region are well described in standard ASTM E544-75, which was reapproved in 1988.

Like the olfactometer described in the standard ASTM E544-75, the olfactometers found in the prior art are generally made from standard laboratory parts. The parts often contain glass and are heavy, fragile and energy consuming. These early suprathreshold designs were either using bottled reference gases, or were generating their own reference gas by passing an odorless gaseous medium over the surface of volatile liquid substance or by bubbling the odorless gaseous medium into the liquid. An example of such olfactometer is disclosed in Sweeten J. et al., Journal of the Air Pollution Control Association, Volume 34, No. 12, pp 1208–1213, December 1984. The construction of an olfactometer controlling a reference gas in an accurate and reliable manner from standard components was requiring performance compromises in lieu of complex and bulky devices. In spite of all efforts, these devices generally require analytical apparatuses for monitoring their proper operation.

More recent olfactometers have reference gas generating systems which are immersed into a liquid bath with a controlled temperature for minimizing the effect of the temperature of the gaseous medium on the partial pressure of the volatile liquid substance. An example of such device is disclosed in U.S. Pat. No. 4,934,386 (Walker et al.) issued on Jun. 19, 1990. However, the olfactometers with a liquid bath are not suitable for fully portable olfactometers.

Until now, the reference odor was provided to the panelists through a plurality of sniffing ports having respective concentrations and continuous flow of the reference odor, or through a single sniffing port where the reference odor is generally diluted by a factor of 2. A reason for this is the lack of reliable reference gas generators in which the concentration of the vapors of the volatile reference substance is known and maintained. It is not relevant to try to obtain precise dilution factors if the reference gas cannot be controlled adequately. Things become worse for portable equipment, as many of the standard laboratory apparatus cannot be incorporated into transportable equipment, be it glass parts, liquid baths, or calibration and analytical instruments that were teamed with most of the previous art olfactometers. The present invention is believed to resolve that problem.

SUMMARY OF THE INVENTION

The object of the present invention is to provide an apparatus for controlling the concentration of the vapors of a volatile liquid substance in a reference gas with good precision and a relative insensibility to the temperature or the flow of a gaseous medium. More particularly, the object of the present invention is to provide an apparatus for generating a reference gas consisting of a gaseous medium carrying a known concentration of vapors of a volatile liquid substance, the apparatus comprising:

an evaporator for mixing the gaseous medium and the vapors into a mixed gas, the evaporator comprising:
an absorbing material filled with the volatile liquid substance; and
a container for enclosing the absorbing material, the container comprising a gaseous medium inlet and a mixed gas outlet;
a condenser for cooling the mixed gas to a given temperature lower than the temperature of the mixed gas in the container and condensing a part of the vapors in the mixed gas, the condenser comprising:
a condensation tube having a first end connected to the mixed gas outlet of the container and a second end as a reference gas outlet, the tube extending above the container so that condensates of the vapors fall by gravity towards the container;
cooling means for cooling at least a portion of the tube;
sensing means for obtaining a signal proportional to the temperature of the mixed gas at the reference gas outlet; and means for controlling the cooling means and maintaining the mixed gas at the reference gas outlet at the given temperature, the means for controlling the cooling means being responsive to the signal of the sensing means.

The object of the present invention is also to provide a method for generating a reference gas consisting of a gaseous medium carrying a known concentration of vapors of a volatile liquid substance, the method comprising the steps of:

introducing the gaseous medium into a container enclosing an absorbing material filled with the volatile liquid substance for obtaining a mixed gas;

cooling the mixed gas with a condenser to a given temperature lower than the temperature of the mixed gas in the container and condensing a part of the vapors so that condensates of the vapors fall by gravity towards the container;

obtaining a signal proportional to the temperature of the mixed gas at an outlet of the condenser; and controlling the cooling of the mixed gas in response to the signal for maintaining the mixed gas at the outlet at the given temperature.

The apparatus and the method according to the present invention are particularly useful in suprathreshold odor olfactometers, gas calibrators and in medicine for evaluating the odor perception of a person.

A non restrictive description of a preferred embodiment will now be given with reference to the appended drawings.

DESCRIPTION OF A PREFERRED EMBODIMENT

Figure 1:
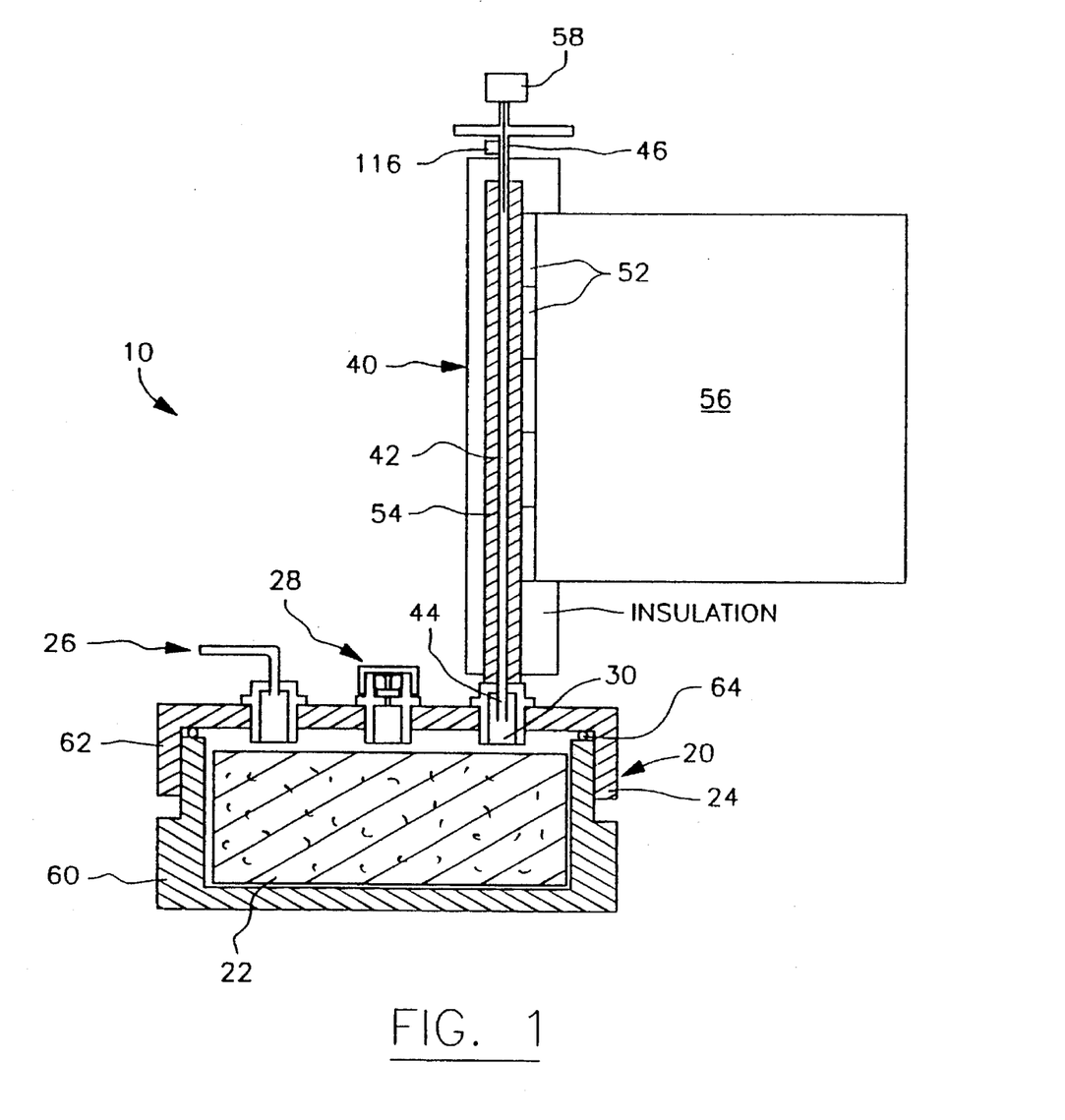
FIG. 1 is an elevational view of the apparatus according to the present invention.

Referring to FIG. 1, the apparatus 10 is provided for producing a reference gas consisting of a gaseous medium carrying a known concentration of vapors of a volatile liquid substance. Such apparatus 10 may also be called a "saturator".

The apparatus 10 comprises an evaporator 20 for mixing the gaseous medium and the vapors, emanating from the volatile liquid substance, into a mixed gas. The evaporator 20 comprises an absorbing material 22 enclosed in a container 24. The container 24 is hermetical to the ambient air and only the gaseous medium goes inside the container 24 through an inlet 26. The gaseous medium, such as nitrogen, is provided in a compressed-gas cylinder or by a suitable filtration equipment. In olfactometry, the gaseous medium should be odorless and may be provided in a portable compressed-gas cylinder in the case of portable olfactometers if the sites where the tests are conducted are not likely to provide a good source of odorless gas without extensive filtration equipment. Some additional filtrations of the gaseous medium prior to its insertion in the apparatus 10 may be required for removing gas impurities and dust. The gaseous medium may be any other gas or mixture of gases suitable for the intended use of the apparatus 10, with the additional requirement of achieving a good chemical compatibility with both the volatile substance and the materials used in the apparatus 10.

The absorbing material 22 is filled with the volatile liquid substance previously injected through a leak-tight port 28 for preventing contamination with foreign matters able to alter the substance. The absorbing material 22 is preferably permeable to the gaseous medium for allowing a good evaporation of the substance. However, complete saturation of the gaseous medium is not absolutely mandatory when the mixed gas leaves the container 24 through the mixed gas outlet 30. Of course, the absorbing material 22 and the container 24 are made with materials not likely to alter the properties to the substance. The ability of the absorbing material 22 to become wet with the liquid substance is also important when designing the apparatus 10.

As described in the standard ASTM E544-75, a very suitable reference odorant is 1-butanol because of its clearly experienceable specific odor. An example of a suitable absorbing material 22 is a borosilicate wool. The container 24 may be made of high-purity alumilium.

The mixed gas produced by the evaporator 20 is then sent to the condenser 40 for cooling mixed gas to a given temperature lower than the temperature of the mixed gas in the container 24. The resulting effect of cooling the mixed gas containing the gaseous medium saturated or almost saturated with vapors of the substance is the condensation of a part of the vapors inside the condenser, indicating that the mixed gas is then completely saturated with the substance. By knowing the mixed gas temperature at the outlet of the condenser and since the mixed gas is saturated, it is possible to determine with great precision the concentration of the substance in ppm. This concentration is a function of the partial vapor pressure of the volatile substance, which itself is a function of the temperature, and the total gas pressure at the evaporator outlet. Typically, the mixed gas is cooled at a temperature about 0° C. Relationships between temperature and partial vapor pressure of substances can be found in standard chemical books, or can be experimentally established in laboratory.

The condenser 40 comprises a condensation tube 42 having a first end 44 connected to the mixed gas outlet 30 and a second end 46 as the apparatus outlet. The tube 42 extends above the container 24 so that condensates of the vapors that are generated therein fall by gravity towards the container 24. The tube 42 is preferably vertical but it may also be inclined. High-purity aluminum is an example of a suitable material if the substance is 1-butanol.

Cooling means are provided for cooling at least a portion of the tube 42 which, in return, cools the mixed gas therein. The cooling means preferably comprises an array of thermoelectric cells 52, which are solid state heat pumps that utilize the Peltier effect. Another advantage of using Peltier cells 52 is that they may be used as heaters during cleaning process. Heating the condenser 40 helps removing residues of the volatile liquid substance.

Preferably, a heat-conducting sleeve 54 is inserted around the tube 42 and the Peltier cells 52 are aligned with each other on one side of the sleeve 54. The sleeve 54 allows a more uniform distribution of the temperature between the tube 42 and the cells 52. The other sides of the sleeve 54 are insulated for improving the thermal stability of the system and for preventing condensation of the ambient humidity on the sleeve 54. A thermal paste, such the ones used in power semiconductors, may be used between the tube 42 and the sleeve 54 for removing air and optimizing the thermal transfer.

Heat transfer means, such as the cooling fins 56, may be provided for dissipating the heat from the hot side of the cells 52. The choice of a proper heat dissipating method can be determined by the use of guidelines provided by the thermoelectric cell and heat sink manufacturer's data books.

Because the temperature of the mixed gas at the outlet 46 has to be substantially equal to a given value, the apparatus 10 is provided with sensing means for obtaining a signal proportional to the temperature of the mixed gas at the outlet 46, and means for controlling the cells 52 and maintaining the mixed gas at the outlet 46 at tile given temperature. The means for controlling the cells 52 and the sensing means form a feedback system so that the means for controlling the cells 52 is responsive to the signal of the sensing means as explained hereinafter. The sensing means comprises a temperature probe 58 at the outlet 46.

Figure 2:
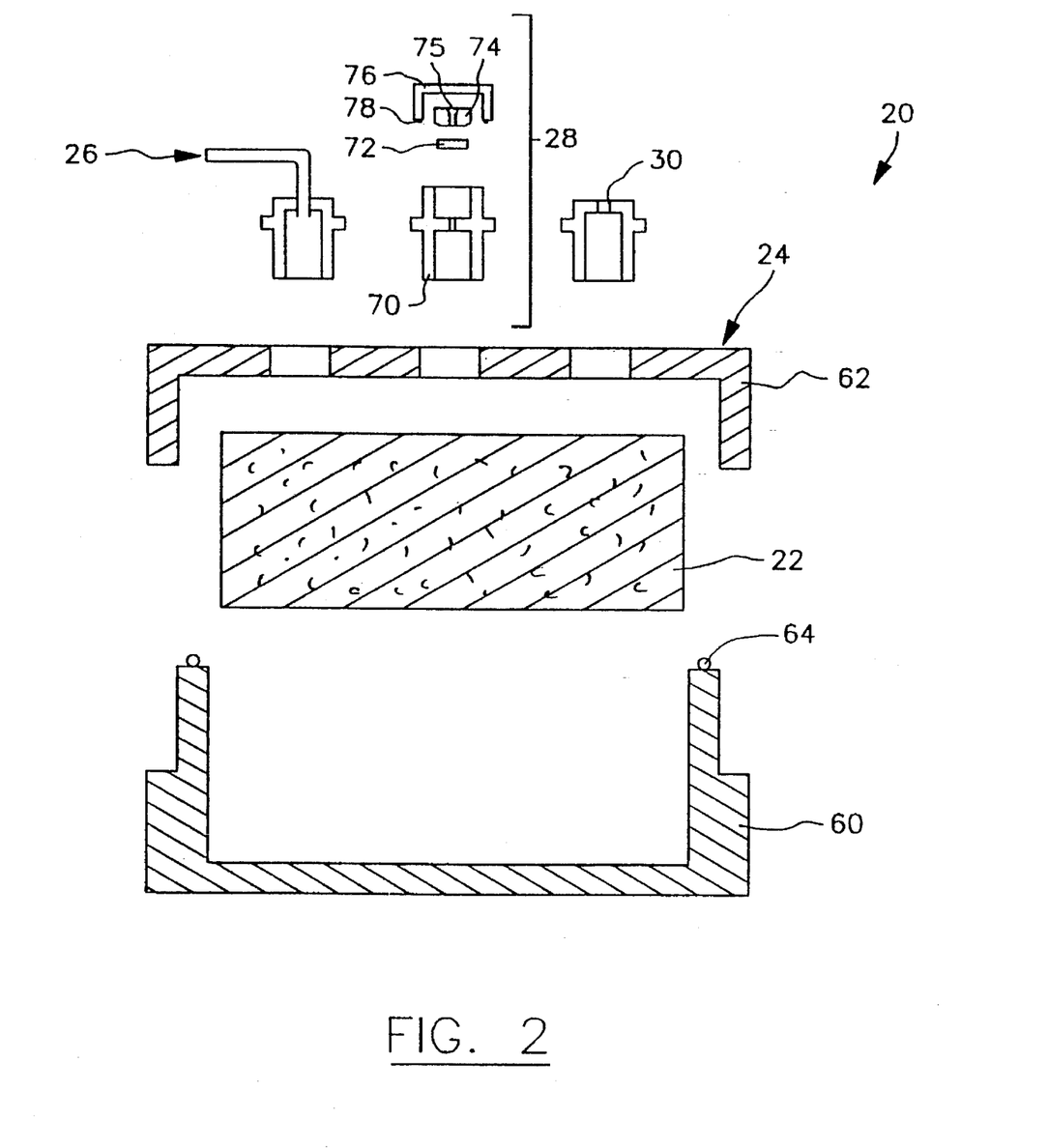
FIG. 2 is an exploded view of the container and the leak-tight port shown in FIG. 1.

FIG. 2 shows an example of the construction of the container 24. This container 24 comprises a hollow part 60 on which is screwed a lid 62. A gasket 64, made of an inert material such as fluorocarbonate, seals the hollow part 60 to the lid 62. As aforesaid, the container 24 is made of a material which is not likely to chemically react with the volatile liquid substance. The interior of tile container 24 is preferably polished for easying the cleaning thereof.

The lid 62 typically comprises three holes. The first hole is the gaseous medium inlet 26, the second hole is for receiving the leak-tight port 28, and the third hole is the mixed gas outlet 30. The first hole and the third hole are diametrically opposed so that the gaseous medium may go through a maximum volume of contact. The position of the second hole is less important since the volatile liquid substance will soak the absorbing material 22 by capillarity.

FIG. 2 also shows an example of construction of a leak-tight port 28 through which the substance in a liquid state is injectable by using a syringe (not shown). This leak-tight port 28 is also important if the substance is likely to chemically react with the oxygen in the ambient air. The port 28 comprises an adaptor 70 screwable to the second hole of the lid 62 and supporting a septum 72 penetrable with the needle of the syringe (not shown), as used in chromatography. A plug 74 with a funnel-shaped hole 75 is set inside of the adaptor 70 for guiding the needle of the syringe. Finally, a cap 76 is provided with a gasket 78 for further sealing the port 28 and keeping it clean.

Figure 3:
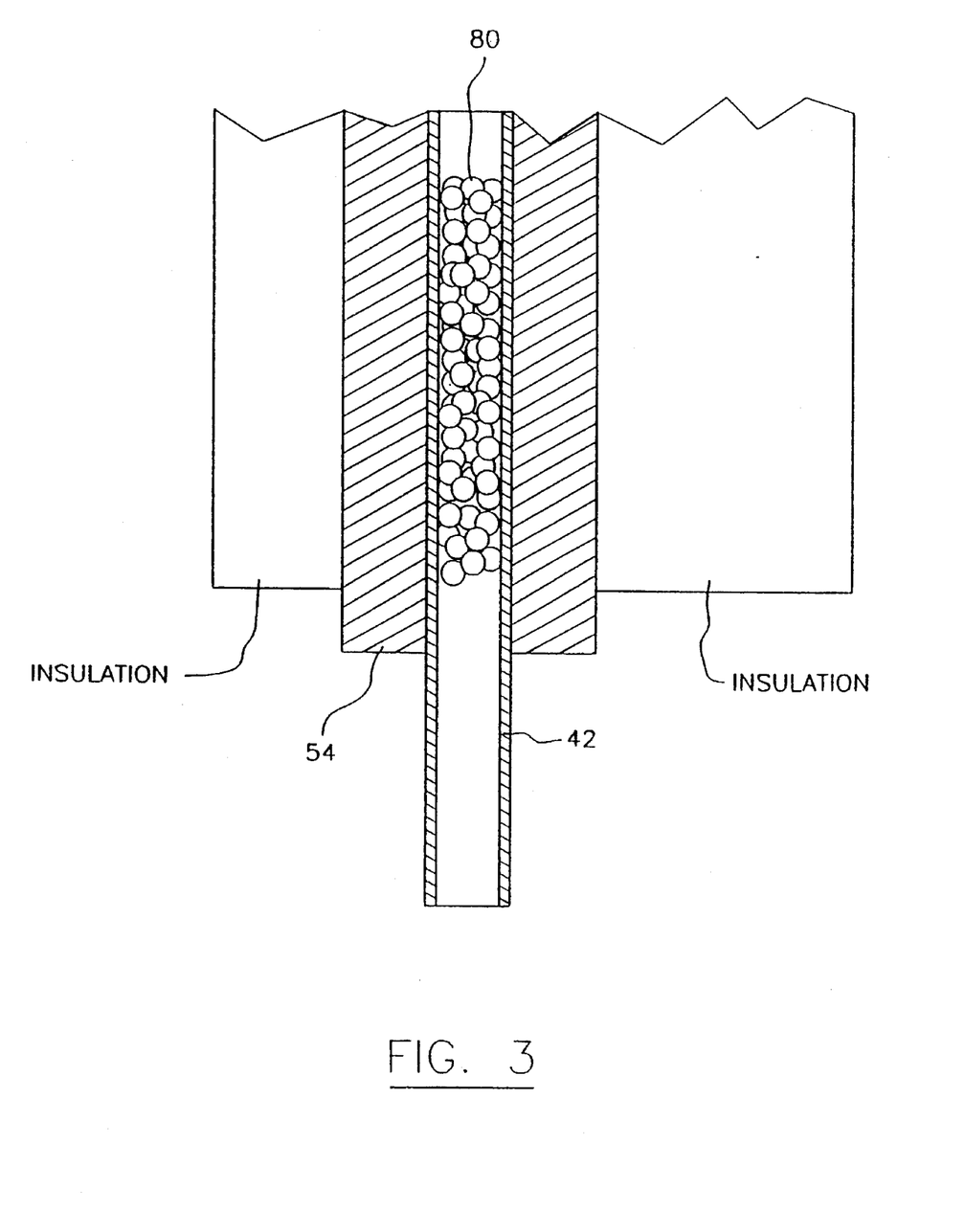
FIG. 3 is a partial enlarged view of the condensation tube according to a preferred embodiment of the present invention, showing the plurality of small balls provided for improving the heat transfer.

As shown in FIG. 3, the tube 42 may comprise means for increasing the heat exchange contact surface, such as a packed bed made of a plurality of chemically inert but heat conductive balls 80. The tube 42 is connected to the container 24 by a Teflon® fitting (not shown), which is known in the art as being generally chemically inert and thermally insulating.

Figure 4:
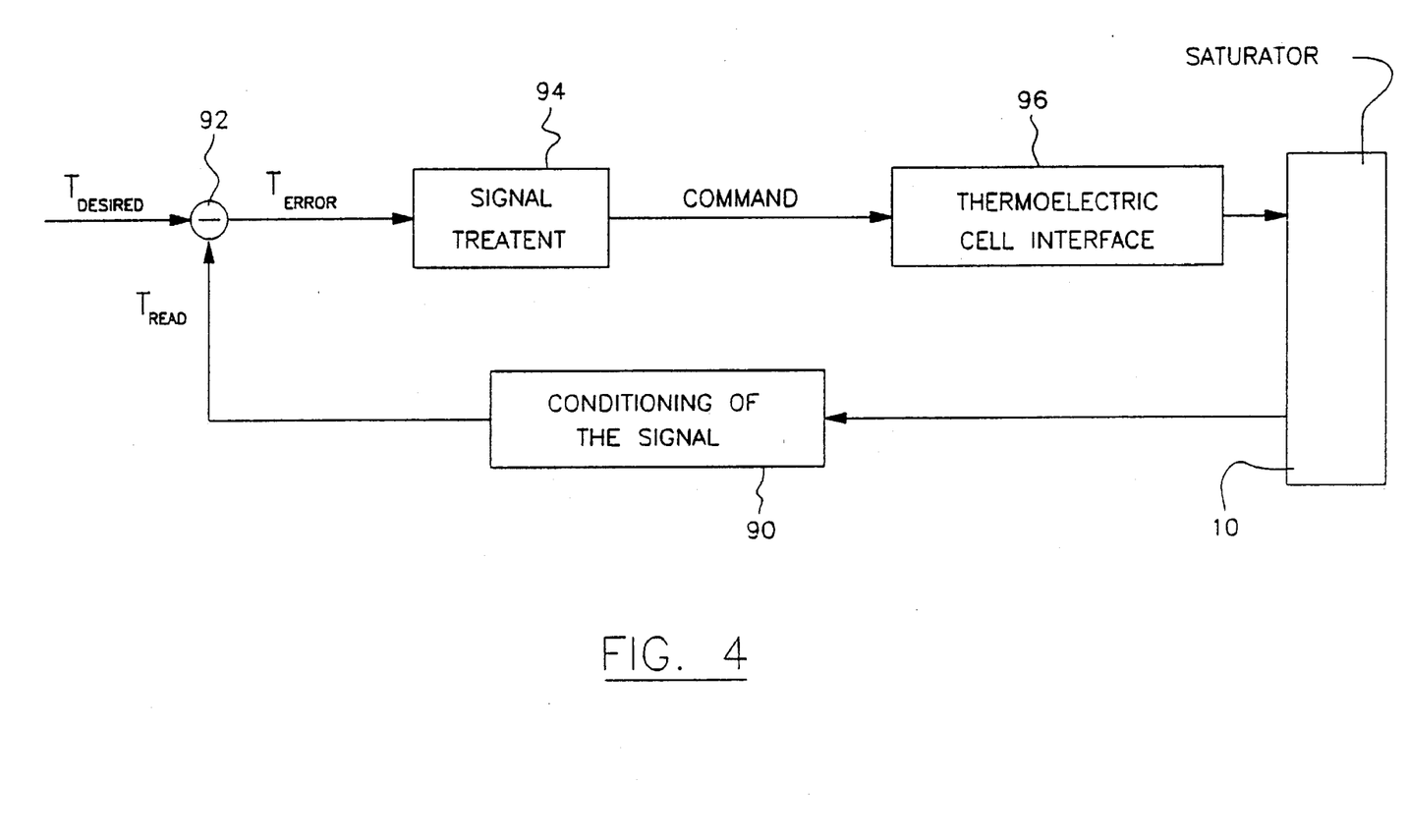
FIG. 4 is a block diagram showing the means for controlling the cooling means and maintaining the mixed gas at the outlet at a given temperature, according to the present invention.

FIG. 4 shows the block diagram representing the means for controlling the cooling means and maintaining the mixed gas at the outlet 46 at a given temperature. This means is substantially a feedback system with a closed loop for regulating the cells 52. The system comprises two entries, the first being the given temperature at which the mixed gas has to remain at the outlet 46 and the second being the temperature read by the probe 58. The signal from the probe 58 is transformed by a signal conditioning module 90 into a signal readable and subtractable with the signal corresponding to the given temperature. The subtraction is achieved by a subtraction module 92 and the resulting signal gives a direct indication of the correction that has to be done for maintaining the mixed gas at the outlet 46 at the given temperature. The resulting signal is thus sent to a calculation module 94 commanding the power supply 96 of the cells 52. An apparatus built along the above described guidelines will be able to achieve the function of generating a known concentration of vapors of a volatile substance with a good insensibility to the flow of the carrier gas and to its incoming temperature. Its predictability will also reduce the need to use continuous gas monitoring instruments, and its relatively small size and ruggedness allows its use in a portable instrument. The components of the means for controlling the cells 52 may be integrated to a computer 120 (FIG. 5) for the automation of the whole process.

The apparatus 10 will require a given preheating time before reaching the full operability. Given the low thermal inertia of the condenser tube and its sleeve, the time needed to reach the temperature setpoint can be achieved in several minutes, which is magnitudes lower than setup times of liquid baths and temperature chambers. Furthermore, the fast setup time of the apparatus 10 allows an additional way to control the mixed gas concentration by varying the temperature setpoint. The effect is that the concentration of the vapors generated by the apparatus 10 can be changed under user control while still keeping its features of insensitiveness to carrier gas flow and temperature.

The present invention is also directed to a corresponding method for producing a reference gas as described hereinabove. The method comprises the steps of introducing the gaseous medium into a container enclosing an absorbing material filled with the volatile liquid substance for obtaining a mixed gas. The mixed gas is then cooled with a condenser to a given temperature lower than the temperature of the mixed gas in the container and condensing a part of the vapors of the substance so that condensates of the vapors fall by gravity towards the container. Monitoring the temperature of the mixed gas at the outlet of the condenser allows control of the cooling means for maintaining the mixed gas at the outlet of the condenser at the given temperature.

Figure 5:
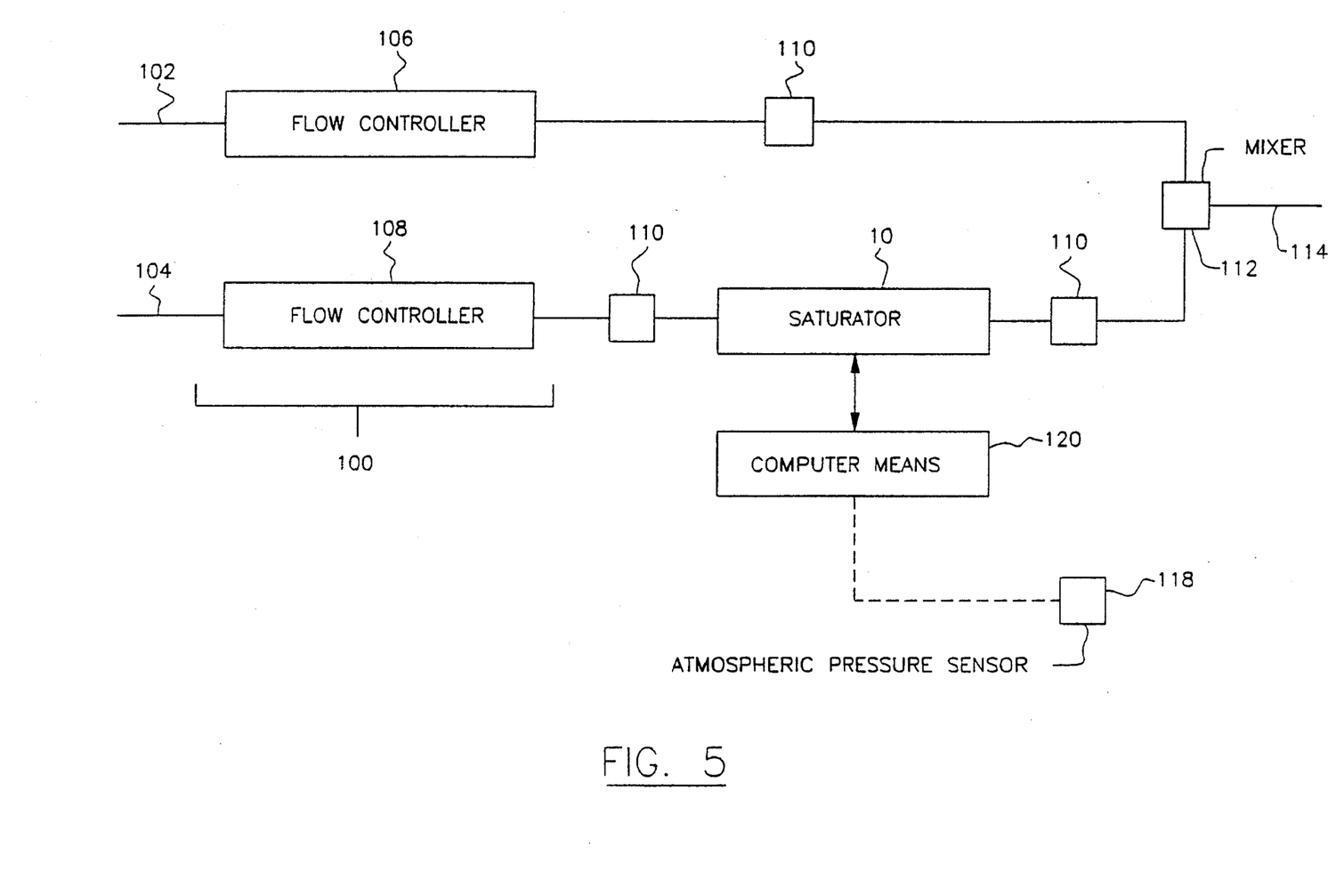
FIG. 5 is a block diagram showing an implement that is useful for the apparatus of FIG. 1.

Referring now to FIG. 5, there is shown a block diagram of the construction of the apparatus 10 with an additional implement 100. In the implement 100, the gaseous medium is provided by two conduits 102 and 104. Both conduits 102 and 104 comprise a respective flow controller 106 and 108. Some valves 110 are present for preventing leaks when the apparatus 10 is not operated. Combined with the leak-tight port 28, all the parts in contact with the reference vapors are kept sealed. This allows the volatile liquid in the container to be protected against degradation due to contact with the oxygen from air. As a part of a portable equipment, this feature allows to clean, fill the container and verify the performance of the equipment prior to its on-site use. No dismantling is necessary when the apparatus 10 is used outside in less than perfect cleanliness conditions, thus increasing the confidence in the results. In use, the conduit 102 will provide a source of gaseous medium that can be mixed with the reference gas produced by the basic components of the apparatus 10. By knowing the flow of the reference gas and its concentration, it is possible to dilute it with different amounts of gaseous medium in the mixer 112 for obtaining different concentrations of gas at the outlet 114, typically ranging, using 1-butanol for instance, from 0,05 to a few hundreds ppm.

Alternatively, it is possible to vary the cooling temperature of the Peltier cells 52 for varying the concentration of the volatile substance.

In a suprathreshold olfactometry application, the invention becomes especially useful as the flow of gas at the outlet 114 has to remain constant while the vapor concentration has to vary. The insensibility of the apparatus to the flow of carrier gas allows this feature to be implemented easily, making it a function of two equations with two variables to determine the rate of the gases flowing in the conduits 102 and 104. The equations for calculating the concentrations at a constant flow are:

(1) $C_{out} = C_{calc} \times F_{condenser}/(F_{condenser} + F_{dilution})$ (2) $F_{condenser} + F_{dilution} = F_{requested}$ where:

$C_{out}$ is the requested concentration at the outlet of the system.

$C_{calc}$ is the concentration of the volatile liquid substance in function of its partial vapor pressure at the given temperature.

$F_{condenser}$ is the flow needed in conduit 104 for the mixed gas in the condenser.

$F_{dilution}$ is the flow needed in conduit 102 for diluting the mixed gas.

$F_{requested}$ is the requested constant total flow.

Such function can be easily resolved by the computer 120, which, when the temperature controlling means of the apparatus 10 is also made by the same computer means, allows for an automation of the instrument. The addition of a pressure sensor 116, at the outlet 46, will give the information needed to compensate for the back pressure caused by the gas flowing through the conduits from the outlet 46 up to the atmosphere and thus calculate a correct vapor concentration value. This value is the one needed for olfactometry purposes. The equation for compensating for the back pressure in the conduits is:

(3) $C_{atm} = C_{calc} \times (P_{atm}/P_{condenser})$ where:

$C_{atm}$ is the concentration of the volatile substance in the mixed gas at the outlet 114;

$C_{calc}$ is the concentration of the volatile substance as calculated in function of its partial vapor pressure at the temperature of the condenser;

$P_{atm}$ is the ambient pressure as measured with pressure sensor 118;

$P_{condenser}$ is the absolute pressure of the mixed gas at the outlet.

As aforesaid, this feature can be easily automated through the computer 120.

In conclusion, the present invention provides an apparatus that is easily portable, thereby allowing on-site odor evaluation where it is most desirable. The stabilization time is very fast compared with other devices in the art. The temperature of the mixed gas at the outlet of the apparatus can be easily changed, thereby providing an extensive range of concentrations. Moreover, the use of an analytical instrument for monitoring the concentration of the mixed gas is not mandatory because of the high precision of the apparatus. Degradation of both the substance and system components is minimum and the variation of the concentration of the volatile liquid substance is predictable and dependable.

In addition to gas calibration and olfactometry, the present invention may be used in medicine for precise evaluation of the odor perception of a person.

Although a preferred embodiment of the invention has been described in detail herein and illustrated in the accompanying drawings, it is to be understood that the invention is not limited to this precise embodiment and that various changes and modifications may be effected therein without departing from the scope or spirit of the invention.

What is claimed is:

1. An apparatus for generating a reference gas comprising a gaseous medium carrying a known concentration of vapors of a volatile liquid substance, the apparatus comprising:

an evaporator for mixing the gaseous medium and the vapors into a mixed gas, the evaporator comprising:
an absorbing material filled with the volatile liquid substance; and
a container for enclosing the absorbing material, the container comprising a gaseous medium inlet and a mixed gas outlet;

a condenser for cooling the mixed gas to a given temperature lower than the temperature of the mixed gas in the container and condensing a part of the vapors in the mixed gas, the condenser comprising:
a condensation tube having a first end connected to the mixed gas outlet of the container and a second end as a reference gas outlet, the tube extending above the container so that condensates of the vapors fall by gravity towards the container;

cooling means for cooling at least a portion of the tube;

sensing means for obtaining a signal proportional to the temperature of the mixed gas at the reference gas outlet; and means for controlling the cooling means and maintaining the mixed gas at the reference gas outlet at the given temperature, the means for controlling the cooling means being responsive to the signal of the sensing means.

2. An apparatus according to claim 1, wherein the absorbing material is permeable to the gaseous medium for increasing the evaporation surface of the volatile liquid substance.

3. An apparatus according to claim 1, further comprising a heat-conducting sleeve enclosing the condensation tube.

4. An apparatus according to claim 3, wherein the cooling means comprises an array of thermoelectric cells.

5. An apparatus according to claim 1, wherein the condensation tube is a high-purity aluminium tube extending substantially vertically over the container.

6. An apparatus according to claim 5, wherein the condensation tube comprises means for increasing the heat exchange capacity of said condensation tube.

7. An apparatus according to claim 6, wherein the means for increasing the heat exchange capacity comprises a packed bed having plurality of thermal conductive balls.

8. An apparatus according to claim 1, wherein the volatile liquid substance is 1-butanol for use in an olfactometer, the gaseous medium being an odorless gas.

9. An apparatus according to claim 8, wherein the absorbing material is a borosilicate wool.

10. An apparatus according to claim 1, wherein the volatile liquid substance is inserted into the container through a leak-tight port.

11. An apparatus according to claim 1, further comprising dilution means for diluting a known quantity of the reference gas with a known quantity of additional gaseous medium.

12. An apparatus according to claim 1, further comprising:

a pressure sensor for monitoring the ambient pressure and generating a first corresponding signal;

a pressure sensor for monitoring the total gas pressure at the outlet of the apparatus and generating a second corresponding signal; and computer means receiving the first and second signals from the pressure sensors and calculating the concentration of the volatile liquid substance in the mixed gas at ambient pressure.

13. An apparatus according to claim 12, wherein the computer means further control a plurality of elements for automation of the apparatus.

14. An apparatus according to claim 1, further comprising valves for operatively sealing the evaporator from ambient air.

15. A method for generating a reference gas comprising a gaseous medium carrying a known concentration of vapors of a volatile liquid substance, the method comprising the steps of:

introducing the gaseous medium into a container enclosing an absorbing material filled with the volatile liquid substance for obtaining a mixed gas;

cooling the mixed gas with a condenser to a given temperature lower than the temperature of the mixed gas in the container and condensing a part of the vapors so that condensates of the vapors fall by gravity towards the container;

obtaining a signal proportional to the temperature of the mixed gas at an outlet of the condenser; and controlling the cooling of the mixed gas in response to the signal for maintaining the mixed gas at the outlet at the given temperature.

16. A method according to claim 15, further comprising the step of varying the given temperature to change the partial vapor pressure of the volatile liquid substance for controlling the concentration of the volatile liquid substance in the mixed gas.

17. A method according to claim 15, further comprising the step of calculating the concentration of the volatile liquid substance in the mixed gas at ambient pressure.

18. A method according to claim 15, further comprising the step of heating the condenser for removing residues of the volatile liquid substance.

19. A method according to claim 15, further comprising the steps of:

diluting the mixed gas with additional gaseous medium for obtaining a precise concentration of volatile substance therein;

providing the diluted mixed gas to a panelist for evaluation of an odor intensity.

20. A method according to claim 15, further comprising the steps of:

diluting the mixed gas with additional gaseous medium for obtaining a precise concentration of volatile substance therein;

providing the diluted mixed gas to a person for evaluating the odor perception of intensity by that person.

* * * * *